US008668915B2

(12) United States Patent
Braun et al.

(10) Patent No.: US 8,668,915 B2
(45) Date of Patent: Mar. 11, 2014

(54) PROCESS FOR THE PREPARATION OF INVERSE LATEX OF ACRYLAMIDE-BASED POLYMERS AND COMPOSITION COMPRISING SAID LATEX

(75) Inventors: Olivier Braun, Castres (FR); Paul Mallo, Croissy-sur-Seine (FR); Audrey Bonnardel, Castres (FR); Francois Guy, Launaguet (FR)

(73) Assignees: Societe d'Exploitation de Produits pour les Industries Chimiques SEPPIC, Paris (FR); Scott Bader Company Limited, Wellingborough (GB)

( * ) Notice: Subject to any disclaimer, the term of this patent is extended or adjusted under 35 U.S.C. 154(b) by 479 days.

(21) Appl. No.: 12/746,817

(22) PCT Filed: Dec. 5, 2008

(86) PCT No.: PCT/EP2008/066863
§ 371 (c)(1),
(2), (4) Date: Jun. 8, 2010

(87) PCT Pub. No.: WO2009/074513
PCT Pub. Date: Jun. 18, 2009

(65) Prior Publication Data
US 2010/0272661 A1    Oct. 28, 2010

(30) Foreign Application Priority Data

Dec. 11, 2007 (EP) ..................................... 07301660

(51) Int. Cl.
| A61K 8/00 | (2006.01) |
| A61K 8/18 | (2006.01) |
| A61Q 17/04 | (2006.01) |
| C08L 33/06 | (2006.01) |
| C09B 67/00 | (2006.01) |

(52) U.S. Cl.
USPC ........ 424/401; 424/70.11; 524/547; 524/543; 524/555; 524/609; 524/610; 524/612; 524/700; 524/801; 524/804; 524/814; 524/817; 524/827; 524/850; 524/881; 524/853; 523/337; 523/336

(58) Field of Classification Search
USPC ......... 524/547, 543, 555, 609, 610, 612, 700, 524/801, 804, 814, 817, 827, 850, 853, 524/881; 523/336, 337; 424/401, 59, 70.11
See application file for complete search history.

(56) References Cited

U.S. PATENT DOCUMENTS

| 5,670,471 | A | 9/1997 | Amalric et al. |
| 5,888,482 | A | 3/1999 | Amalric et al. |
| 5,958,431 | A | 9/1999 | Brancq et al. |
| 6,245,821 | B1 | 6/2001 | Bulcourt et al. |
| 6,268,400 | B1 | 7/2001 | Amalric et al. |
| 6,353,034 | B1 | 3/2002 | Amalric et al. |
| 6,464,993 | B1 | 10/2002 | Milius et al. |
| 6,488,946 | B1 | 12/2002 | Milius et al. |
| 6,667,396 | B2 | 12/2003 | Milius et al. |
| 6,673,861 | B2 * | 1/2004 | Tabacchi et al. ............... 524/458 |
| 2004/0057986 | A1 * | 3/2004 | Merrigan et al. ............. 424/449 |
| 2007/0219315 | A1 * | 9/2007 | Braun .......................... 524/801 |
| 2007/0265386 | A1 | 11/2007 | Mallo et al. |

FOREIGN PATENT DOCUMENTS

| FR | 2 668 080 A1 | 4/1992 |
| FR | 2 734 496 A1 | 11/1996 |
| FR | 2 756 195 A1 | 5/1998 |
| FR | 2 762 317 A1 | 10/1998 |
| FR | 2 784 680 A1 | 4/2000 |
| FR | 2 784 904 A1 | 4/2000 |
| FR | 2 786 493 A1 | 6/2000 |
| FR | 2 790 977 A1 | 9/2000 |
| FR | 2 791 565 A1 | 10/2000 |
| FR | 2 804 432 A1 | 8/2001 |
| FR | 2 807 435 A1 | 10/2001 |
| FR | 2 873 126 A1 | 1/2006 |
| WO | 92/06778 A1 | 4/1992 |
| WO | 93/08204 A1 | 4/1993 |
| WO | 95/04592 A1 | 2/1995 |
| WO | 95/13863 A1 | 5/1995 |
| WO | 96/37285 A1 | 11/1996 |
| WO | 98/22207 A1 | 5/1998 |
| WO | 98/47610 A1 | 10/1998 |

OTHER PUBLICATIONS

International Search Report, dated Feb. 10, 2009, from corresponding PCT application.

* cited by examiner

*Primary Examiner* — Fereydoun G Sajjadi
*Assistant Examiner* — Alma Pipic
(74) *Attorney, Agent, or Firm* — Young & Thompson

(57) ABSTRACT

Process for the preparation of a an inverse latex including from 20% to 70% by weight and preferably from 25% to 50% by weight of a branched or crosslinked polyelectrolyte, characterized in that the polyelectrolyte is a copolymer of 2-acrylamido-2-methylpropanesulfonic acid partially or totally salified with acrylamide and optionally one or more monomers chosen from monomers containing a partially or totally salified weak acid function and/or from neutral monomers other than acrylamide, the production process including the control of the pH in the initial aqueous phase; Cosmetic, dermopharmaceutical or pharmaceutical composition including the inverse latex directly obtained by the process.

8 Claims, No Drawings

PROCESS FOR THE PREPARATION OF INVERSE LATEX OF ACRYLAMIDE-BASED POLYMERS AND COMPOSITION COMPRISING SAID LATEX

The present patent application relates to a preparation process of a water-in-oil inverse latex, and to the use of the said inverse latex as thickeners and/or emulsifiers for skincare and hair care products or for the manufacture of cosmetic, dermocosmetic, dermopharmaceutical or pharmaceutical preparations.

The thickeners used in the cosmetics or pharmaceutical industry, are intended to thicken aqueous phases, lotions or cream-gels. In the case of cream-gels, an emulsifier is also added, especially when it is desired to incorporate a high content of oil into the formulation. However, emulsifiers are often products with a low molecular weight, which are potentially less tolerated by the skin than polymers. Furthermore, the use of polymers allows the preparation of cream-gels without heating, which reduces the manufacturing costs while at the same time keeping the heat-sensitive molecules, that might be comprised in such cream-gels, intact. Accordingly, it has been sought to develop polymers that are both thickeners and emulsifiers. Among them, reference is made to self-invertible inverse latex of copolymer of 2-acrylamido-2-methyl propanesulfonic acid (AMPS) and acrylamide crosslinked with N,N-methylene bis(acrylamide), partially or totally neutralized in the form sodium or potassium salt, said polymeric inverse emulsion being disclosed in European patent application publication EP 0 503 853 and in International publication WO 01/35922. In both documents the preparation process involves the use of 50 to 60% weight by weight aqueous solution of AMPS sodium salt and acrylamide and the polymerization is made at a pH=7. Such an AMPS sodium salt solution is available as a 55% weight by weight solution at CIM chemicals under the trade name ATB-SNa or as 50% or 58% weight by weight solution at Lubrizol under the respective trade names AMPS2405 and AMPS2405A. Acrylamide is commercially available as a 50% weight by weight acrylamide, or in solid form. Acrylamide monomer can be synthesized by a chemical process from acrylonitrile, which induces the formation of a by-product known as 3,3',3''-nitrilo tris(propionamide). For example, "Acrylamide 50%" commercialized by KEMIRA is prepared according to the process involving the hydrolysis of acrylonitrile under cupric catalysis and therefore implies the activation of such Cu Raney catalyst which is previously treated with alkali under temperature over 100° C. The catalytic reaction is conducted at high temperature (around 100° C.) and in an alkali pH. Acrylamide monomer can also be synthesized by an enzymatic process, which does not induce the formation of such a by-product. For example—"Acrylamide 50 HST" commercialized by SNF, is prepared according to the process involving the hydrolysis of acrylonitrile under enzymatic catalysis (nitril hydratase) and therefore at mild catalytic conditions (20-25° C., neutral pH). Moreover such a by-product is formed when acrylamide in placed in solution in alkaline pH, whatever the manufacturing process is. It has been observed that, depending on the storage conditions and the storage duration, the concentration of acrylamide in some samples of the final polymer composition had increased over a 2 ppm limit until becoming prejudicial to the use of said composition in topical formulations.

That is why, according to a first embodiment, the invention relates to an improved production process of inverse latex of acrylamide based polymers, which avoids acrylamide release in the final composition. According to a more specific aspect, the invention relates to a process for the preparation of a composition comprising an oil phase, an aqueous phase, at least one emulsifying system of the water-in-oil (W/O) type, optionally at least one emulsifying system of the oil-in-water (O/W) type, in the form of an inverse latex comprising from 20% to 70% by weight and preferably from 25% to 50% by weight of a branched or crosslinked polyelectrolyte, characterized in that said polyelectrolyte is a copolymer (P) of 2-acrylamido-2-methylpropanesulfonic acid partially or totally salified in the form of a sodium salt, or of a potassium salt or of an ammonium salt, with acrylamide and optionally one or more monomers chosen from monomers containing a weak acid function partially or totally salified in the form of a sodium salt, or of a potassium salt or of an ammonium salt, and/or from neutral monomers other than acrylamide, said preparation process comprising the following steps:

A Step a) of preparation of an aqueous phase (A) comprising acrylamide 2-acrylamido-2-methylpropanesulfonic acid partially or totally salified in the form of a sodium salt, or of a potassium salt or of an ammonium salt, optionally one or more monomers chosen from monomers containing a weak acid function partially or totally salified in the form of a sodium salt, or of a potassium salt or of an ammonium salt, and/or from neutral monomers other than acrylamide and the possible other hydrophilic additives, said preparation consisting in placing free 2-acrylamido-2-methylpropanesulfonic acid, optionally 2-acrylamido-2-methylpropanesulfonic acid in the form of a sodium salt, or of a potassium salt or of an ammonium salt, acrylamide, said optional hydrophilic additives and, if necessary, an alkaline agent chosen from sodium hydroxide, potassium hydroxide or aqueous ammonia in water, such that the pH of the solution remains greater than 1 and less than 5, to obtain a first aqueous mixture A1 having a pH value greater than to 1 and less than 5; and in adjusting the pH value of said the first aqueous mixture A1 to a pH between 5 and 6.5, to obtain said aqueous phase (A);

A step b) of emulsification of said aqueous phase (A), in an organic phase containing a surfactant system of the water-in-oil (W/O) type, the oil intended to be present in the final composition, optionally a volatile oil, and optional hydrophobic additives, to form a water-in-oil emulsion (B);

A step c) of polymerization of the monomers in said water-in-oil emulsion (B), said reaction being initiated by introducing a free-radical initiator into said emulsion (B), to form an inverse latex (L1) of said copolymer (P);

Optionally a step d), wherein said inverse latex (L1) of said copolymer (P), is concentrated by distillation until the said volatile oil has been removed, to form an inverse latex (L2) of said copolymer (P); and A step e) wherein an emulsifying system of the oil-in-water (O/W) type is introduced, if desired, at a temperature below 50° C., in said inverse latex (L1) of said copolymer (P), or optionally in said inverse latex (L2) of said copolymer (P), to form a self-invertible inverse latex (L3) of said copolymer (P).

The neutral monomers other than acrylamide are especially chosen from methacrylamide, diacetoneacrylamide, N-isopropylacrylamide, N-[2-hydroxy-1,1-bis[(hydroxymethyl)ethyl]]propenamide [or tris(hydroxymethyl)acrylamidomethane or N-tris(hydroxymethyl)methacrylamide also known as THAM], le N,N-dimethylacrylamide, (2-hydroxyethyl)acrylate, (2,3-dihydroxypropyl)acrylate, (2-hydroxyethyl)methacrylate, (2,3-dihydroxypropyl)methacrylate, an ethoxylated derivative with a molecular weight of between 400 and 1000, of each of these esters, or vinylpyrrolidone.

According to a particular embodiment of the process as hereinabove defined in Step e), the emulsifying system of oil-in-water type is introduced at a temperature below 50° C.

According to one preferred embodiment of the process as hereinabove defined, the polymerization reaction of Step c), is initiated with a redox couple, such as the cumene hydroperoxide/sodium metabisulfite couple, at a temperature of less than or equal to 10° C., and is then performed either quasi-adiabatically up to a temperature of greater than or equal to 40° C. and more particularly greater than or equal to 50° C., or by controlling the change of the temperature.

When the composition prepared by the process as hereinabove defined, comprises at least 50% by weight and not more than 70% by weight of polyelectrolyte, said process preferably comprises Step d). In this case, the volatile oils that are suitable for performing the process as hereinabove defined are, are chosen from for example, light isoparaffins containing from 8 to 11 carbon atoms, for instance those sold under the names Isopar™ G, Isopar™ L, Isopar™ H or Isopar™ J.

When the composition as hereinabove defined comprises less than 50% by weight of polyelectrolyte, said process does not generally comprise Step d).

According to one variant of this process, the reaction medium obtained from Step c) is concentrated by distillation, before performing step e).

According to one preferred embodiment of the process as hereinabove defined, the polymerization reaction of Step c), is initiated with a redox couple, such as the cumene hydroperoxide/sodium metabisulfite couple, at a temperature of less than or equal to 10° C., and is then performed either quasi-adiabatically up to a temperature of greater than or equal to 40° C. and more particularly greater than or equal to 50° C., or by controlling the change of the temperature.

According to another particular aspect of the present invention, the composition as hereinabove defined comprises not more than 30% by weight of polyelectrolyte.

According to another particular embodiment of the process as hereinabove defined the polyelectrolyte comprises between 60 mol % and 20 mol % of 2-methyl-2-[(1-oxo-2-propenyl)amino]-1-propanesulfonic acid monomer partially or totally salified in the form of a sodium salt, of a potassium salt or of an ammonium salt and between 40 mol % and 80 mol % of acrylamide monomer.

According to one particular aspect of the present invention, the polyelectrolyte present in the composition comprises between 50 mol % and 30 mol % 2-methyl-2-[(1-oxo-2-propenyl)amino]-1-propanesulfonic acid monomer partially or totally salified in the form of a sodium salt, or of a potassium salt or of an ammonium salt and between 50 mol % and 70 mol % of acrylamide monomer.

According to another particular aspect of the present invention, when the polyelectrolyte present in the composition as hereinabove defined a copolymer (P) of 2-acrylamido-2-methylpropanesulfonic acid partially or totally salified in the form of a sodium salt, or of a potassium salt or of an ammonium salt, of acrylamide and of one or more monomers chosen from monomers containing a weak acid function acid partially or totally salified in the form of a sodium salt, or of a potassium salt or of an ammonium salt and/or neutral monomers other than acrylamide, the mole proportion of all of the monomers chosen from the monomers containing a weak acid function and the neutral monomers other than acrylamide is greater than 0% and less than or equal to 30%. According to this particular aspect, the mole ratio between the acrylamide and all of the monomers chosen from the monomers containing a weak acid function and the neutral monomers other than acrylamide is preferably greater than or equal to 1.

According to another particular embodiment of the process as hereinabove defined, the aqueous mixture A1 obtained at Step (a), has a pH value greater than 1 and less than 4, namely less than 3 and more particularly less than 2.

The term "branched polymer" denotes a non-linear polymer containing side chains so as to obtain, when this polymer is dissolved in water, extensive entanglement leading to very high viscosities at low shear.

The term "crosslinked polymer" denotes a non-linear polymer in the form of a water-insoluble but water-swellable three-dimensional network thus leading to the production of a chemical gel.

The composition according to the invention may comprise a polyelectrolyte comprising crosslinked units and/or branched units.

When the polymer present in the composition that is the subject of the present invention is crosslinked, it is more particularly crosslinked with a diethylenic or polyethylenic compound in a mole proportion, expressed relative to the monomers used, of from 0.005% to 1%, more particularly from 0.010% to 0.20% and still more particularly from 0.015% to 0.15%. Preferably, the crosslinking agent and/or the branching agent is chosen from ethylene glycol dimethacrylate, diethylene glycol diacrylate, sodium diallyloxyacetate, ethylene glycol diacrylate, diallylurea, triallylamine, trimethylolpropane triacrylate and methylenebis (acrylamide).

In the composition as hereinabove defined, the emulsifying system of the water-in-oil (W/O) type, consists either of a sole surfactant or of a mixture of surfactants on condition that the HLB value of the said mixture is low enough to induce water-in-oil emulsions. As emulsifiers of water-in-oil type, there are, for example, sorbitan esters, for instance sorbitan oleate, for instance the product sold by the company SEPPIC under the name Montane™ 80, sorbitan isostearate, for instance the product sold by the company SEPPIC under the name Montane™ 70, or sorbitan sesquioleate, for instance the product sold by the company SEPPIC under the name Montane™ 83. There are also certain polyethoxylated sorbitan esters, for example pentaethoxylated sorbitan monooleate, for instance the product sold by the company SEPPIC under the name Montanox™ 81 or pentaethoxylated sorbitan isostearate, for instance the product sold under the name Montanox™ 71 by the company SEPPIC. There are also certain fatty alkanolamides, for instance oleyldiethanolamide sold under the name of WITCAMIDE™ 511 by the company AKZO-NOBEL. There is also diethoxylated oleocetyl alcohol, for instance the product sold under the name Simulsol™ OC 72 by the company SEPPIC, tetraethoxylated lauryl acrylate, for instance the product sold under the name Blemmer™ ALE 200 or polyesters with a molecular weight of between 1000 and 3000, produced from condensation between a poly(isobutenyl)succinic acid or its anhydride and polyethylene glycol, such as Hypermer™ 2296 sold by the company Uniqema, or, finally, block copolymers with a molecular weight of between 2500 and 3500, for instance Hypermer™ B246 sold by the company Uniqema or Simaline™ IE 200 sold by the company SEPPIC.

The composition that is the subject of the present invention generally comprises from 2% to 8% by weight of emulsifying system of water-in-oil (W/O) type.

In the composition as hereinabove defined, the emulsifying system of the oil-in-water (O/W) type, consists either of a sole surfactant or of a mixture of surfactants on condition that the HLB value of the said mixture is high enough to induce oil-in-water emulsions. As emulsifiers of oil-in-water type, there are, for example, ethoxylated sorbitan esters, for instance sorbitan oleate polyethoxylated with 20 mol of ethylene oxide, sold by the company SEPPIC under the name Montanox™ 80, sorbitan laurate polyethoxylated with 20 mol of ethylene oxide, sold by the company SEPPIC under the name Montanox™ 20, castor oil polyethoxylated with 40 mol of ethylene oxide, sold under the name Simulsol™ OL50, decaethoxylated oleodecyl alcohol, sold by the company SEPPIC under the name Simulsol™ 00710, heptaethoxylated lauryl alcohol, sold under the name Simulsol™ P7 or sorbitan monostearate polyethoxylated with 20 mol of ethylene oxide, sold by the company SEPPIC under the name Montanox™ 60.

The composition that is the subject of the present invention generally comprises from 3% to 8% by weight of emulsifying system of oil-in-water (O/W) type.

In the composition that is the subject of the present invention, the oil phase comprises a commercial mineral oil containing saturated hydrocarbons, for instance paraffins, isoparaffins or cycloparaffins, having at room temperature a density of between 0.7 and 0.9 and a boiling point of greater than about 250° C., for instance Marcol™ 52, Isopar™ M or Isopar™ L sold by Exxon Chemical; isohexadecane, identified in Chemical Abstracts by the number RN=93685-80-4, which is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9); it is sold in France by the company Bayer, or isododecane also sold in France by the company Bayer; or a synthetic oil such as hydrogenated polydecene or hydrogenated polyisobutene, sold in France by the company Ets B. Rossow et Cie under the name Parleam-Polysynlane™. It is cited in: Michel and Irene Ash; Thesaurus of Chemical Products, Chemical Publishing Co. Inc. 1986 Volume I, page 211 (ISBN 0 7131 3603 0); or a plant oil, for instance squalane of plant origin sold in France by the company Sophim, under the name Phytosqualane™ and identified in Chemical Abstracts by the number RN=111-01-3; it is a mixture of hydrocarbons containing more than 80% by weight of 2,6,10,15,19,23-hexamethyltetracosane, or of a mixture of several of these oils.

The oil phase may also comprise fatty acid esters. In the context of the present invention, the term "fatty acid ester" means a compound of formula (I):

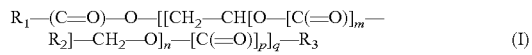

in which:

$R_1$ represents a saturated or unsaturated, linear or branched hydrocarbon-based chain containing from 7 to 30 carbon atoms, $R_2$ represents, independently of $R_1$, a hydrogen atom or a saturated or unsaturated, linear or branched hydrocarbon-based chain containing from 7 to 30 carbon atoms, $R_3$ represents, independently of $R_1$ or $R_2$, a hydrogen atom or a saturated or unsaturated, linear or branched hydrocarbon-based chain containing from 1 to 30 carbon atoms, m, n, p and q are, independently of each other, equal to 0 or 1, it being understood that when $R_3$ represents a hydrogen atom, q is other than 0.

In the formula (I) as hereinabove defined, $R_1$, $R_2$ and $R_3$ especially represent, independently of each other, a radical chosen from heptyl, octyl, nonyl, decyl, undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl, docosenyl, heptadecadienyl and decenyl radicals; the group $R_1$—C(=O)— more particularly represents one of the following radicals: octanoyl(caprylyl), decanoyl, undecylenoyl, dodecanoyl(lauroyl), tetradecanoyl (myristyl), hexadecanoyl(palmitoyl), octadecanoyl(stearyl), eicosanoyl(arachidoyl), docosanoyl(behenoyl), 8-octadecenoyl(oleyl), eicosenoyl(gadoloyl), 13-docosenoyl(erucyl), 9,12-octadecadienoyl(linoleoyl), 9,12,15-octadecatrienoyl (linolenoyl).

The oil phase may more particularly comprise a compound of formula (Ia):

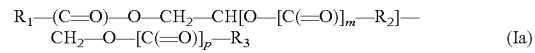

corresponding to formula (I) as hereinabove defined in which q and n are equal to 1, or a mixture of compounds of formula (Ia). In this case, it is preferably
either a compound of formula (Ia₁):

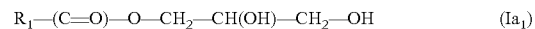

corresponding to formula (Ia) as hereinabove defined in which m and p are equal to 0 and $R_2$ and $R_3$ represent a hydrogen atom,
or a compound of formula (Ia₂):

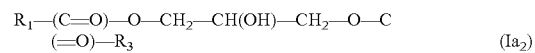

corresponding to formula (Ia) as hereinabove defined in which p is equal to 1, m is equal to 0 and $R_2$ represents a hydrogen atom,
or a compound of formula (Ia₃):

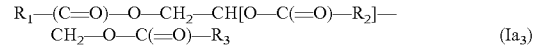

corresponding to formula (Ia) as hereinabove defined in which m and p are equal to 1,
or a mixture of compounds of formulae (Ia₁), (Ia₂) and/or (Ia₃).

As examples of compounds of formula (Ia₁), (Ia₂) or (Ia₃), there are, for example, fatty acid triglycerides or fatty acid mixtures such as the mixture of fatty acid triglycerides containing from 6 to 10 carbon atoms, sold under the name Softenol™ 3819, the mixture of fatty acid triglycerides containing from 8 to 10 carbon atoms, sold under the name Softenol™ 3108, the mixture of fatty acid triglycerides containing from 8 to 18 carbon atoms, sold under the name Softenol™ 3178, the mixture of fatty acid triglycerides containing from 12 to 18 carbon atoms, sold under the name Softenol™ 3100, the mixture of fatty acid triglycerides containing 7 carbon atoms, sold under the name Softenol™ 3107, the mixture of fatty acid triglycerides containing 14 carbon atoms, sold under the name Softenol™ 3114, or the mixture of fatty acid triglycerides containing 18 carbon atoms, sold under the name Softenol™ 3118, glyceryl dilaurate, glyceryl dioleate, glyceryl isostearate, glyceryl distearate, glyceryl monolaurate, glyceryl monooleate, glyceryl monoisostearate or glyceryl monostearate, or a mixture of these compounds.

The oil phase may more particularly comprise a compound of formula (Ib):

corresponding to formula (I) as hereinabove defined in which q is equal to 0, or a mixture of compounds of formula (Ib).

An example of a compound of formula (Ib) is, for example, octyl palmitate.

The inverse latex as hereinabove defined generally contains from 4% to 10% by weight of emulsifiers. Its oil phase generally represents from 15% to 40% and preferably from 20% to 25% of the total weight of the composition. The aqueous phase generally represents from 2% to 40% of the total weight of the composition.

According to another particular aspect of the present invention, a subject thereof is a composition obtained by the process, as hereinabove defined in which the copolymer is chosen from:

crosslinked copolymers of 2-methyl-2-[(1-oxo-2-propenyl)amino]-1-propanesulfonic acid partially salified in the form of the sodium salt and of acrylamide;

crosslinked copolymers of 2-methyl-2-[(1-oxo-2-propenyl)amino]-1-propanesulfonic acid partially salified in the form of the ammonium salt and of acrylamide;

crosslinked copolymers of 2-methyl-2-[(1-oxo-2-propenyl)amino]-1-propanesulfonic acid partially salified in the form of the potassium salt and of acrylamide;

crosslinked terpolymers of 2-methyl-2-[(1-oxo-2-propenyl)amino]-1-propanesulfonic acid partially salified in the form of the sodium salt, of the potassium salt or of the ammonium salt, of acrylic acid partially salified in the form of the sodium salt, the potassium salt or the ammonium salt and of acrylamide;

crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of N,N-dimethylacrylamide and of acrylamide;

crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of acrylamide;

crosslinked terpolymers of 2-methyl-2-[(1-oxo-2-propenyl)amino]-1-propanesulfonic acid partially salified in the form of the sodium salt, the potassium salt or the ammonium salt, of acrylamide and of N-isopropylacrylamide;

crosslinked terpolymers of 2-methyl-2-[(1-oxo-2-propenyl)amino]-1-propanesulfonic acid partially salified in the form of the sodium salt, the potassium salt or the ammonium salt, of acrylamide and of N-[2-hydroxy-1,1-bis(hydroxymethyl)ethyl]propenamide;

crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of acrylamide and of (2-hydroxyethyl)acrylate;

crosslinked terpolymers of 2-methyl-2-[(1-oxo-2-propenyl)amino]-1-propanesulfonic acid partially salified in the form of the sodium salt, the potassium salt or the ammonium salt, of acrylamide and of (2-hydroxyethyl)acrylate.

A subject of the invention is also a cosmetic, dermopharmaceutical or pharmaceutical composition, characterized in that it comprises as thickening and/or emulsifying compound at least one inverse latex obtained by the process, as hereinabove defined. The cosmetic, dermocosmetic, dermopharmaceutical or pharmaceutical composition hereinabove defined generally comprises from 0.1% to 10% and more particularly between 0.5% and 5% by weight of the said inverse latex. It is especially in the form of a water-in-oil emulsion, an oil-in-water emulsion, a water-in-oil-in-water emulsion, an oil-in-water-in-oil emulsion, a milk, a lotion, a gel, a cream-gel, a cream, a soap, a bubblebath, a balm, a shampoo or a conditioner. According to one preferred aspect of the present invention, the cosmetic, dermocosmetic, dermopharmaceutical or pharmaceutical composition as hereinabove defined is a topical composition.

A subject of the invention is also the use of the inverse latex obtained by the process, as hereinabove defined for preparing a cosmetic, dermopharmaceutical or pharmaceutical topical composition. The topical composition according to the invention, intended to be applied to the skin or mucous membranes of man or animals, may consist of a topical emulsion comprising at least one aqueous phase and at least one oil phase. This topical emulsion may be of the oil-in-water type. More particularly, this topical emulsion may consist of a fluid emulsion, such as a milk or a fluid gel. The oil phase of the topical emulsion may consist of a mixture of one or more oils. A topical composition according to the invention may be intended for cosmetic use or may be used to prepare a medicament for treating skin and mucous membrane diseases. In the latter case, the topical composition then comprises an active principle that may consist, for example, of an anti-inflammatory agent, a muscle relaxant, an antifungal agent or an antibacterial agent.

The compositions according to the invention may also contain ingredients usually used in the cosmetic and dermopharmaceutical fields and known to those skilled in the art, such as fats (oils, butters, waxes, fatty acids and gums), emulsifiers and coemulsifiers, gelling agents and/or stabilizers and/or film-forming agents, fillers, pigments, sunscreens, humectants, solvents and cosolvents, plasticizers, sequestrants, antioxidants, fragrances, preserving agents or active principles. As examples of oils that may be combined with the composition of the invention, mention may be made of paraffins, isoparaffins, white mineral oils, plant oils, animal oils, synthetic oils, silicone oils and fluoro oils; and more particularly:

oils of plant origin, such as sweet almond oil, coconut oil, castor oil, jojoba oil, olive oil, rapeseed oil, groundnut oil, sunflower oil, wheatgerm oil, corn germ oil, soybean oil, cottonseed oil, alfalfa oil, poppyseed oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sysymbrium oil, avocado oil, calendula oil and floral or legume oils; ethoxylated plant oils; oils of animal origin, such as squalene and squalane; mineral oils, such as liquid paraffin, liquid petroleum jelly and isoparaffins; synthetic oils, especially fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, for instance glyceryl triheptanoate, alkylbenzoates, poly-α-olefins, polyolefins, for instance polyisobutene, synthetic isoalkanes, for instance isohexadecane, isododecane, perfluoro oils and silicone oils. Among the silicone oils, mention may be made more particularly of dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As another fatty substance that may be combined with the composition of the invention, mention may be made of fatty alcohols or fatty acids.

The fatty phase of the preparations according to the invention may also contain waxes such as beeswax; carnauba wax; candelilla wax, ouricury wax; japan wax; cork fibre wax or sugarcane wax; paraffin waxes; lignite waxes; microcrystalline waxes; lanolin wax; ozokerite; polyethylene wax; hydrogenated oils; silicone waxes; plant waxes; fatty alcohols and fatty acids that are solid at room temperature; glycerides that are solid at room temperature.

The inverse latex according to the invention may optionally be combined with other thickening and/or emulsifying polymers. Examples that may be mentioned include homopolymers or copolymers of acrylic acid or of acrylic acid derivatives, homopolymers or copolymers of acrylamide, homopolymers or copolymers of acrylamide derivatives, homopolymers or copolymers of acrylamidomethyl propanesulfonic acid, of vinyl monomer, of trimethylaminoethyl acrylate chloride sold under the names Carbopol™ Ultrez™ 10, Pemulen™ TR1, Pemulen™ TR2, Simulgel™ A, Simulgel™ NS, Simulgel™ EPG, Simulgel™ EG, Luvigel™ EM, Salcare™ SC91, Salcare™ SC92, Salcare™ SC95, Salcare™ SC96, Flocare™ ET100, Hispagel™, Sepigel™ 305, Sepigel™ 501, Sepigel™ 502, Sepiplus™ 265, Sepiplus™ 400, Sepiplus™ S, Sepinov™ EMT 10, Flocare™ ET58 and Stabileze™ 06; hydrocolloids of plant or biosynthetic origin, for instance xanthan gum, karaya gum, carrageenates or alginates; silicates; cellulose and its derivatives; starch and its hydrophilic derivatives; polyurethanes.

The composition according to the invention is also an advantageous substitute for those sold under the names Sepigel™ 305, Sepigel™ 501, Simulgel™ EG, Simulgel™ NS or Simulgel™ 600 by the Applicant, since it also shows good compatibility with the other excipients used for the preparation of formulations such as milks, lotions, creams, creamgels, soaps, bubblebaths, balms, shampoos or hair conditioners. It is especially compatible with the concentrates described and claimed in the international publications WO 92/06778, WO 95/04592, WO 95/13863, WO 96/37285, WO 98/22207, and WO 98/47610 or in FR 2 734 496, with the surfactants described in WO 93/08204.

Among the emulsifiers that may be used in the presence of the inverse latex according to the invention, examples that may be mentioned include fatty acids; ethoxylated fatty acids; fatty acid esters of sorbitol; ethoxylated fatty acid esters; polysorbates; polyglycerol esters; ethoxylated fatty alcohols; sucrose esters; alkylpolyglycosides; sulfated or phosphated fatty alcohols or mixtures of alkylpolyglycosides and of fatty alcohols described in French patent applications 2 668 080, 2 734 496, 2 756 195, 2 762 317, 2 784 680, 2 784 904, 2 791 565, 2 790 977, 2 807 435 and 2 804 432, Sensanov™ WR and Fluidanov™20X.

The cosmetic, dermocosmetic, dermopharmaceutical or pharmaceutical composition as hereinabove defined may also comprise texture agents and/or fillers, for instance acrylic and methacrylic acid copolymers, starches, silicas, calcium, magnesium, aluminum or barium silicates, calcium phosphate, natural fibres such as cotton fibre, cellulose fibre or chitosan fibre, or synthetic fibres such as polyamide (Nylon®) fibre, rayon fibre, viscose fibre, cellulose acetate fibre, poly-p-phenylene-terephthamide fibre (Kevlar®), polyethylene or polypropylene fibre, glass fibre, carbon fibre, Teflon fibre, polyester fibre, polyvinyl chloride fibre, polyvinyl alcohol fibre, polyacrylonitrile fibre, polyurethane fibre or polyethylene phthalate fibre, talc, mica, sericite, silica, boron nitride, lauroyl lysine, silicone resin powders, calcium carbonate, magnesium carbonate, titanium oxide, zinc oxide or cerium oxide, titanium micas, iron oxides and other mineral or organic pigments, or a mixture of these powders.

As examples of active principles that may be combined with the inverse latex according to the invention, mention may be made of compounds with a lightening or depigmenting action, a moisturizing action, a tensioning action, a calmative or relaxing action, a purifying, seboregulatory or hair-loss-countering action, an anti-ageing action, or a firming, restructuring action, a free-radical-scavenging action, an antioxidant action or a self-tanning action. The composition of the invention may thus be combined with active agents such as, for example, arbutin, kojic acid, hydroquinone, ellagic acid, vitamin C and its derivatives, Stay C, magnesium ascorbyl phosphate and its derivatives, ascorbyl glucoside, phytic acid, fruit acids, lactic acid, rucinol or resorcinol, azeleic acid, glycolic acid, gluconic acid, dihydroxyacetone (DHA), erythrulose, lipoic acid, Vegewhite™, Gatuline™, Synerlight™, Biowhite™, Phytolight™, Dermalight™, Clariskin™, Melaslow™, Dermawhite™, Ethioline™, Melarest™, Gigawhite™, Albatine™, Lumiskin™, polyphenol extracts, grape extracts, pine extracts, wine extracts, olive extracts, tea extracts, cocoa extracts, Amazonian forest plant extracts, legume extracts, floral extracts, fruit extracts, mint extracts, pond extracts, N-acyl proteins, N-acyl peptides, for instance Matrixyl™, N-acylamino acids, partial hydrolysates of N-acyl proteins, amino acids, peptides, total protein hydrolysates, partial protein hydrolysates, polyols (for instance glycerol, butylene glycol, etc.), milk derivatives, Aquaxyl™, urea, pyrrolidonecarboxylic acid or derivatives of this acid, glycyrrhetinic acid or its derivatives, α-bisabolol, sugars or sugar derivatives, polysaccharides or derivatives thereof, hydroxy acids, for instance lactic acid or salicylic acid, vitamins, vitamin derivatives, for instance retinol, retinol derivatives, vitamin E and its derivatives, minerals, trace elements, extracts of rocks or stones, enzymes or derivatives thereof, coenzymes or derivatives thereof, for instance coenzyme Q10, hormones or "hormone-like" substances, for instance Phyto Age™, soybean extracts, for instance Raffermine™, wheat extracts, for instance Tensine™ or Gliadine™, plant extracts, tannin-rich plant extracts, isoflavone-rich extracts or terpene-rich extracts, freshwater or saltwater algal extracts, marine extracts in general, including coral extracts, essential waxes, bacterial extracts, minerals, for instance the range of Givobio™ products and especially the calcium, magnesium, copper, cobalt, zinc, manganese, etc. derivatives, lipids in general, lipids such as ceramides or phospholipids and also derivatives, active agents with a slimming action, for instance caffeine or its derivatives, active agents that improve the capillary circulation of the skin, for instance venotonic agents, draining active agents, decongestive active agents such as ginko biloba, ivy, common horsechestnut, bamboo, ruscus, centella asiatica, fucus, rosemary or sage, active agents with antimicrobial activity or a purifying action on greasy skin, for instance copper or zinc derivatives or octopirox or Sensiva SC50, active agents with energizing or stimulating properties, for instance Sepitonic™ M3 or Physiogenyl™, panthenol and its derivatives, for instance Sepicap™ MP, anti-ageing active agents, Sepivinol™, Sepivital™, Manoliva™ and Phytoage™. The composition of the invention may also more generally be combined with anti-ageing active agents for combating photoageing, the targeted active agents protecting the integrity of the dermo-epidermal junction, active agents that increase the synthesis of components of the extracellular matrix (for instance collagen, elastins, glycosaminoglycans, etc.), active agents that act favorably on chemical (cytokines) or physical (integrins) cell communication, active agents with a restructuring effect, active agents with a cicatrizing effect, active agents with a firming effect, active agents with a "botox-like" effect, active agents that act on expression wrinkles, active agents that act on the calcium channels, active agents that improve the integrity of the skin barrier, active agents that act on specific skin enzymes, active agents that act on specific cell receptors, active agents that improve cell communication, active agents with a free-radical-scavenging or antioxidant effect, active agents with a "tensioning" effect and active agents with an antidandruff, anti-acne, calmative or anti-neuromediator effect. The composition containing the polymer according to the invention may also be combined with active agents that afford a heating effect on the skin, such as skin capillary circulation activators (for example nicotinates) or ingredients that create, conversely, a sensation of freshness on application (for example menthol).

As sunscreens that may be incorporated with the composition of the invention, mention may be made of any of those featured in the amended Cosmetic Directive 76/768/EEC appendix VII. According to this preferred aspect, the sunscreen is more particularly chosen from lipophilic sunscreens, for instance octocrylene, etocrylene, homosalate, for instance Eusolex™ HMS, octyl para-methoxycinnamate, for instance Parsol™ MCX, octinoxate, octisalate, avobenzone, oxybenzone, benzophenone-1, benzophenone-2, benzophenone-3, for instance Uvinul M-40, benzophenone-8, benzophenone-12, ethyl dihydroxypropyl PABA, glyceryl PABA, ethylhexyl dimethyl PABA, menthyl anthranilate, methylbenzylidenecamphor or isopropyl dibenzoyl methane. The sunscreen as hereinabove defined may also comprise one or more lipophobic sunscreens, for instance titanium dioxide, zinc oxide, phenylbenzimidazolesulfonic acid, benzophenone-4, TEA salicylate, PABA and DEA methoxycinnamate. The sunscreen as hereinabove defined may also comprise one or more oil absorbers, for instance silica, whether these are spherical silicas, for instance Spheron™ L-1500, porous silica or pyrogenic silica, crosslinked or non-crosslinked polymethyl methacrylate, for instance the Micropearl™ products, dextrins, cyclodextrins, molecular sieves, for instance zeolites, Nylon™ 6 or 12, sodium calcium aluminosilicate, talc or mica. The sunscreen as hereinabove defined may also comprise one or more esters of neopentanoic acid with an isoalkyl alcohol containing from 10 to 22 carbon atoms. In this case, it preferably comprises isodecyl neopentanoate, isostearyl neopentanoate or isoarachidyl neopentanoate.

According to a particular aspect of the invention, the cosmetic, dermopharmaceutical or pharmaceutical composition comprises an efficient quantity of dihydroxyacetone and more particularly between 1% and 8% by weight of the composition of dihydroxyacetone. According to a more particular aspect of the invention, the cosmetic, dermopharmaceutical or pharmaceutical composition comprises either dihydroxyacetone and at least a hydroxy acid such as lactic acid, salicylic acid, gluconic acid or kojic acid, either dihydroxyacetone and at least one sunscreen agent, either dihydroxyacetone and at least one moisterizing agent, either dihydroxyacetone and at least on slimming agent such as caffeine.

The examples that follow are intended to illustrate the present invention without, however, limiting it.

EXAMPLE 1

Preparation of a Polymer Composition According to the Inventive Process

Step 1: Preparation of the Aqueous Phase
254 g of a commercial solution containing 50% acrylamide, commercialized under the trade name of "Acrylamide 50 HST™" by SNF, is introduced into a vessel equipped with a mechanical stirrer, at a temperature of 17° C.

247.32 g of an aqueous solution containing 55% by weight 2-methyl-2-[(1-oxo-2-propenyl)amino]-1-propanesulfonic acid sodium salt, commercialized under the trade name of ATBS 55% by CIM Chemicals, is then introduced and the pH is measured at a value of 6.0.

A quantity of 123 g of 2-methyl-2-[(1-oxo-2-propenyl) amino]-1-propanesulfonic acid under powder form, commercialized under the trade name of ATBS G from Toagosei, is introduced by fractions of 12.3 g alternatively with fractions of 9.54 g of a sodium hydroxide solution in 50%, the total amount of such 50% sodium hydroxide being of 95.4 g at the end of such fractional additions. The pH is controlled between each addition of the ATBS G fractions and sodium hydroxide fractions and measured values were recorded in a pH range between 1.8 and 2.2. At the end of such addition, the pH is measured at 2.2 and then additional sodium hydroxide solution is added in order to achieved a pH value of this aqueous phase at 6.0. 0.45 g of sodium diethylenetriaminepentaacetate and 0.107 g of methylenebis(acrylamide) are then added to the previously prepared aqueous media and the pH is again controlled at a value of 6.0. The aqueous phase weight is finally adjusted at 682 g by addition of water.

Step 2: Preparation of the Organic Phase
An organic phase is prepared by mixing together in a separate vessel equipped with a mechanical stirrer:
220 g of Isopar™ M (C13-C14 isoparaffin),
25.0 g of Witcamide™ 511 (partially esterified N,N-dialkanolamide),
These components are mixed at 20° C. with a mechanical stirrer at a low speed of 80 rounds per minute for 15 minutes.

Step 3: Preparation of the Monomer Emulsion
The aqueous phase is gradually introduced into the organic phase and the mixture is stirred vigorously using a Silverson™ or IKA™ stirrer, for example.

Step 4: Preparation of the Polymer Emulsion
The emulsion obtained is then transferred into a polymerization reactor, sparged with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 ml/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. The reaction medium is then cooled and when the temperature of and the resulting compound reaches 25° C., 50 g Laureth™ 7 is added to obtain the expected inverse latex.

Evaluation of the Properties of the Polymer Composition

Viscosity of the inverse latex at 2% by weight in de-ionized water (Brookfield RVT):
μ=82 800 mPa·s; pH=6.1
Viscosity of the inverse latex at 2% by weight in de-ionized water+0.1% NaCl (Brookfield RVT): μ=30 200 mPa·s;

Preparation of an Aqueous Gel with the Polymer Composition of Example 1

98 g of deionized water are introduced into a 250 mL beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel. The beaker containing the aqueous gel prepared as previously described is placed into a regulated oven at a temperature of 75° C. For each measurement of the acrylamide concentration, 5 g of the previously prepared gel, stored into the oven, are introduced into a 10 mL graduated flask at room temperature, with 1 g of sodium chloride under powder form. A saturated solution of sodium chloride is then added into the graduated flask in order to adjust the volume of the solution to 10 mL. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 75° C. as well as after 48 h at 75° C., it is observed that the acrylamide concentration brought back to the starting inverse latex, stays under 2 ppm and does not increase along the time.

COMPARATIVE EXAMPLE 1

Preparation of a Polymer Composition According to the Process According to the State of the Art Step 1: Preparation of the Aqueous Phase 254 g of a commercial solution containing 50% acrylamide, commercialized under the trade name of "Acrylamide 50 HST" by SNF, is introduced into a vessel equipped with a mechanical stirrer, at a temperature of 17° C. 95.4 g of a 50% sodium hydroxide is then added into the vessel containing the acrylamide solution and stirred at 20° C. The pH is measured at a value of 13.8. 246 g of 2-methyl-2-[(1-oxo-2-propenyl)amino]-1-propanesulfonic acid in powder form, commercialized under the trade name of ATBS G from Toagosei, is progressively added in order to maintain a temperature into the vessel under 25° C. At the end of such addition, the pH of this aqueous phase is adjusted at 6.0. 0.45 g of sodium diethylenetriaminepentaacetate and 0.107 g of methylene-bis(acrylamide) are then added to the previously prepared aqueous media and the pH is again controlled at a value of 6.0. The aqueous phase weight is finally adjusted at 682 g by addition of water.

Step 2: Preparation of the Organic Phase

An organic phase is prepared by mixing together in a separate vessel equipped with a mechanical stirrer:
220 g of Isopar™ M (C13-C14 isoparaffin),
25 g of Witcamide™ 511(partially esterified N,N-dialkanolamide), These components are mixed at 20° C. with a mechanical stirrer at a low speed of 80 rounds per minute for 15 minutes.

Step 3: Preparation of the Monomer Emulsion

The aqueous phase is gradually introduced into the organic phase and the mixture is stirred vigorously using a Silverson™ or IKA™ stirrer, for example.

Step 4: Preparation of the Polymer Emulsion

The emulsion obtained is then transferred into a polymerization reactor, sparged with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 ml/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. The reaction medium is then cooled and when the temperature of and the resulting compound reaches 25° C., 50 g Laureth™ 7 is added to obtain the expected inverse latex.

Evaluation of the Properties of the Polymer Composition

Viscosity of the inverse latex at 2% by weight in de-ionized water (Brookfield RVT):
μ=99 000 mPa·s; pH=6.3
Viscosity of the inverse latex at 2% by weight in de-ionized water+0.1% NaCl (Brookfield RVT): μ=30 000 mPa·s;

Preparation of an Aqueous Gel with the Polymer Composition of Comparative Example 1

98 g of deionized water are introduced into a 250 mL beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel.

The beaker containing the aqueous gel prepared as previously described is placed into a regulated oven at a temperature of 75° C. For each measurement of the acrylamide concentration, 5 g of the previously prepared gel, stored into the oven, are introduced into a 10 mL graduated flask at room temperature, with 1 g of sodium chloride under powder form. A saturated solution of sodium chloride is then added into the graduated flask in order to adjust the volume of the solution to 10 mL. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 75° C. it is observed that the acrylamide concentration brought back to the starting inverse latex, increases until 15 ppm and after 48 h at 75° C., reaches 31 ppm.

COMPARATIVE EXAMPLE 2

Preparation of a Polymer Composition According to the Process According to the State of the Art Step 1: Preparation of the Aqueous Phase 254 g of a commercial solution containing 50% acrylamide, commercialized under the trade name of "Acrylamide 50%" by KEMIRA, is introduced into a vessel equipped with a mechanical stirrer, at a temperature of 17° C. 95.4 g of a 50% sodium hydroxide is then added into the vessel containing the acrylamide solution and stirred at 20° C. The pH is measured at a value of 13.8. 246 g of 2-methyl-2-[(1-oxo-2-propenyl)amino]-1-propanesulfonic acid in powder form, commercialized under the trade name of ATBS G from Toagosei, is progressively added in order to maintain a temperature into the vessel under 25° C. At the end of such addition, the pH of this aqueous phase is adjusted at 6.0. 0.45 g of sodium diethylenetriaminepentaacetate and 0.107 g of methylenebis(acrylamide) are then added to the previously prepared aqueous media and the pH is again controlled at a value of 6.0. The aqueous phase weight is finally adjusted at 682 g by addition of water.

Step 2: Preparation of the Organic Phase

An organic phase is prepared by mixing together in a separate vessel equipped with a mechanical stirrer:

220 g of Isopar™ M (C13-C14 isoparaffin), 25 g of Witcamide™ 511(partially esterified N,N-dialkanolamide), These components are mixed at 20° C. with a mechanical stirrer at a low speed of 80 rounds per minute for 15 minutes.

Step 3: Preparation of the Monomeric Emulsion

The aqueous phase is gradually introduced into the organic phase and the mixture is stirred vigorously using a Silverson™ or IKA™ stirrer, for example.

Step 4: Preparation of the Polymeric Emulsion

The emulsion obtained is then transferred into a polymerization reactor, sparged with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 ml/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. The reaction medium is then cooled and when the temperature of and the resulting compound reaches 25° C., 50 g Laureth™ 7 is added to obtain the expected inverse latex.

Evaluation of the Properties of the Polymer Composition

Viscosity of the inverse latex at 2% by weight in de-ionized water (Brookfield RVT):

µ=95 000 mPa·s; pH=6.3

Viscosity of the inverse latex at 2% by weight in de-ionized water+0.1% NaCl (Brookfield RVT): µ=32 000 mPa·s;

Preparation of an Aqueous Gel with the Polymer Composition of Comparative Example 2

98 g of deionized water are introduced into a 250 mL beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel. The beaker containing the aqueous gel prepared as previously described is placed into a regulated oven at a temperature of 75° C. For each measurement of the acrylamide concentration, 5 g of the previously prepared gel, stored into the oven, are introduced into a 10 mL graduated flask at room temperature, with 1 g of sodium chloride under powder form. A saturated solution of sodium chloride is then added into the graduated flask in order to adjust the volume of the solution to 10 mL. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 75° C. it is observed that the acrylamide concentration brought back to the starting inverse latex, increases until 60 ppm and after 48 h at 75° C., reaches 100 ppm.

COMPARATIVE EXAMPLE 3

Preparation of a Polymer Composition According to the Process According to the State of the Art Step 1: Preparation of the Aqueous Phase 254 g of a commercial solution containing 50% acrylamide, commercialized under the trade name of "Acrylamide 50%" by KEMIRA, is introduced into a vessel equipped with a mechanical stirrer, at a temperature of 17° C.

247.32 g of an aqueous solution containing 55% by weight 2-methyl-2-[(1-oxo-2-propenyl)amino]-1-propanesulfonic acid sodium salt, commercialized under the trade name of ATBS 55% by CIM Chemicals, is then introduced and the pH is measured at a value of 1.4.

A quantity of 123 g of 2-methyl-2-[(1-oxo-2-propenyl)amino]-1-propanesulfonic acid under powder form, commercialized under the trade name of ATBS G from Toagosei, is introduced by fractions of 12.3 g alternatively with fractions of 9.54 g of a sodium hydroxide solution in 50%, the total amount of such 50% sodium hydroxide being of 95.4 g at the end of such fractional additions. The pH is controlled between each addition of the ATBS G fractions and sodium hydroxide fractions and measured values were recorded in a pH range between 1.8 and 2.2. At the end of such addition, the pH is measured at 2.2 and then additional sodium hydroxide solution is added in order to achieved a pH value of this aqueous phase at 6.0. 0.45 g of sodium diethylenetriaminepentaacetate and 0.107 g of methylenebis(acrylamide) are then added to the previously prepared aqueous media and the pH is again controlled at a value of 6.0. The aqueous phase weight is finally adjusted at 682 g by addition of water.

Step 2: Preparation of the Organic Phase

An organic phase is prepared by mixing together in a separate vessel equipped with a mechanical stirrer:

220 g of Isopar™ M (C13-C14 isoparaffin), 25 g of Witcamide™ 511(partially esterified N,N-dialkanolamide), These components are mixed at 20° C. with a mechanical stirrer at a low speed of 80 rounds per minute for 15 minutes.

Step 3: Preparation of the Monomeric Emulsion

The aqueous phase is gradually introduced into the organic phase and the mixture is stirred vigorously using a Silverson™ or IKA™ stirrer, for example.

Step 4: Preparation of the Polymeric Emulsion

The emulsion obtained is then transferred into a polymerization reactor, sparged with nitrogen and then cooled to about 5-6° C. 10 g of a solution containing 0.5 g sodium persulfate is then added, followed, after homogenization of the solution, by addition of an aqueous solution of sodium metabisulfite (2.5% by weight in water) at a rate of 0.5 ml/minute for about 60 minutes, while allowing the temperature to rise at the end of polymerization. The reaction medium is then maintained for about 90 minutes at this temperature. Sodium metabisulfite is then added in order to obtain an acrylamide concentration in the final composition, less than 2 ppm. The reaction medium is then cooled and when the temperature of and the resulting compound reaches 25° C., 50 g Laureth™ 7 is added to obtain the expected inverse latex.

Preparation of an Aqueous Gel with the Polymer Composition of Comparative Example 3

98 g of deionized water are introduced into a 250 mL beaker and stirred at room temperature with mechanical stirrer equipped with an anchor modulus at 50 rpm. 2 g of the inverse latex as previously prepared, are progressively added into the stirred deionized water. The aqueous media thickens and a gel is formed. This gel is stirred at room temperature at 80 rpm in order to achieve a homogeneous appearance of such a gel. The beaker containing the aqueous gel prepared as previously described is placed into a regulated oven at a temperature of 75° C. For each measurement of the acrylamide concentration, 5 g of the previously prepared gel, stored into the oven, are introduced into a 10 mL graduated flask at room temperature, with 1 g of sodium chloride under powder form. A saturated solution of sodium chloride is then added into the graduated flask in order to adjust the volume of the solution to 10 mL. The graduated flask containing the diluted gel into the sodium chloride solution is manually stirred. Such a stirred solution of gel in sodium chloride is then filtered off and quantified by the mean of a High Performance Liquid Chromatograph equipped with a Ultra-Violet detector. After 24 h at 75° C. it is observed that the acrylamide concentration brought back to the starting inverse latex, increases until 30-35 ppm and after 48 h at 75° C., reaches 50 ppm. It thus results that the control of the pH of the aqueous phase in Step a) of the claimed process, seems to be a key points to prevent acrylamide releasing in unfriendly storage conditions from the final thickened formulation. Comparison between example 1 and comparative example 3, also shows that the absence of 3,3',3"-nitrilo tris(propionamide) (CAS Number [2664-61-1]) in the starting acrylamide is necessary, when it is needed to reach a maximum of 2 ppm acrylamide in the final formulation.

Examples of Formulations Prepared with the Compositions According to the Invention

EXAMPLE 2

Care Cream

| | | |
|---|---|---|
| Cyclomethicone: | | 10% |
| Inverse latex of Example 1: | | 0.8% |
| Montanov ™ 68: | | 2% |
| Stearyl alcohol: | | 1% |
| Stearyl alcohol: | | 0.5% |
| Preserving agent: | | 0.65% |
| Lysine: | | 0.025% |
| EDTA (disodium salt): | | 0.05% |
| Xanthan gum: | | 0.2% |
| Glycerol: | | 3% |
| Water: | | qs 100% |

EXAMPLE 3

Aftershave Balm

Formula

| A | Inverse latex of Example 1: | 1.5% |
|---|---|---|
| | Water: | qs 100% |
| B | Micropearl ™ M 100: | 5.0% |
| | Sepicide ™ CI: | 0.50% |
| | Fragrance: | 0.20% |
| | 95° ethanol: | 10.0% |

Procedure
  Add B to A.

EXAMPLE 4

Satin Body Emulsion

Formula

| A | Simulsol ™ 165: | 5.0% |
|---|---|---|
| | Lanol ™ 1688: | 8.50% |
| | Shea butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Inverse latex of Example 1: | 3% |
| E | Sepicide ™ CI: | 0.3% |
| | Sepicide ™ HB: | 0.5% |
| | Aquaxyl ™: | 3% |
| | Fragrance: | 0.20% |
| | Vitamin E acetate: | 0.20% |
| | Sodium pyrolidinonecarboxylate: | 1% |

Procedure
  Add C to B, emulsify B in A at 70° C. and then add D at 60° C., followed by E at 30° C.

EXAMPLE 5

Oil-in-Water Cream

Formula

| A | Simulsol ™ 165: | 5.0% |
|---|---|---|
| | Lanol ™ 1688: | 20.0% |
| | Lanol ™ P: | 1.0% |
| B | Water: | qs 100% |
| C | Inverse latex of Example 1: | 2.50% |
| D | Sepicide ™ CI: | 0.20% |
| | Sepicide ™ HB: | 0.30% |

Procedure
  Introduce B into A at about 75° C.; add C at about 60° C., then D at about 45° C.

EXAMPLE 6

Non-Greasy Antisun Gel

Formula

| A | Inverse latex of Example 1: | 3.00% |
|---|---|---|
| | Water: | 30% |
| B | Sepicide ™ CI: | 0.20% |
| | Sepicide ™ HB: | 0.30% |
| | Fragrance: | 0.10% |
| C | Dye: | qs |
| | Water: | 30% |
| D | Micropearl ™ M 100: | 3.00% |
| | Water: | qs 100% |
| E | Silicone oil: | 2.0% |
| | Parsol ™ MCX: | 5.00% |

Procedure
  Introduce B into A; add C, then D, then E.

EXAMPLE 7

Antisun Milk

Formula

| A | Montanov™ S: | 3.0% |
|---|---|---|
|   | Sesame oil: | 5.0% |
|   | Parsol™ MCX: | 5.0% |
|   | Carrageenan λ: | 0.10% |
| B | Water: | qs 100% |
| C | Inverse latex of Example 1: | 0.80% |
| D | Fragrance: | qs |
|   | Preserving agent: | qs |

Procedure
  Emulsify B in A at 75° C. then add C at about 60° C., followed by D at about 30° C., and adjust the pH if necessary.

EXAMPLE 8

Massage Gel

Formula

| A | Inverse latex of Example 1: | 3.5% |
|---|---|---|
|   | Water: | 20.0% |
| B | Dye: | 2 drops/100 g |
|   | Water: | qs |
| C | Alcohol: | 10% |
|   | Menthol: | 0.10% |
| D | Silicone oil: | 5.0% |

Procedure
  Add B to A, then add C to the mixture, followed by D.

EXAMPLE 9

Moisturizing and Matting Foundation

Formula

| A | Water: | 20.0% |
|---|---|---|
|   | Butylene glycol: | 4.0% |
|   | PEG-400: | 4.0% |
|   | Pecosil™ PS100: | 1.0% |
|   | NaOH: | qs pH = 9 |
|   | Titanium dioxide: | 7.0% |
|   | Talc: | 2.0% |
|   | Yellow iron oxide: | 0.8% |
|   | Red iron oxide: | 0.3% |
|   | Black iron oxide: | 0.05% |
| B | Lanol™ 99: | 8% |
|   | Caprylic/capric triglyceride: | 8% |
|   | Montanov™ 202: | 5.00% |
| C | Water: | qs 100% |
|   | Micropearl™ M305: | 2.0% |
|   | Tetrasodium EDTA: | 0.05% |
| D | Cyclomethicone: | 4.0% |
|   | Xanthan gum: | 0.2% |
|   | Inverse latex of Example 1: | 0.8% |
| E | Sepicide™ HB: | 0.5% |
|   | Sepicide™ CI: | 0.3% |
|   | Fragrance: | 0.2% |

Procedure
  Prepare mixtures B+D and A+C at 80° C., then mix together and emulsify the whole.

EXAMPLE 10

Radiance Gel

Formula

| A | Inverse latex of Example 1: | 4% |
|---|---|---|
|   | Water: | 30% |
| B | Elastine HPM: | 5.0% |
| C | Micropearl™ M 100: | 3% |
|   | Water: | 5% |
| D | Sepicide™ CI: | 0.2% |
|   | Sepicide™ HB: | 0.3% |
|   | Fragrance: | 0.06% |
|   | Sodium pyrolidinonecarboxylate 50%: | 1% |
|   | Water: | qs 100% |

Procedure
  Prepare A; add B, then C, then D.

EXAMPLE 11

Body Milk

Formula

| Montanov™ S: | 3.5% |
|---|---|
| Lanol™ 37T: | 8.0% |
| Solagum™ L: | 0.05% |
| Water: | qs 100% |
| Benzophenone-3: | 2.0% |
| Dimethicone 350 cPs: | 0.05% |
| Inverse latex of Example 1: | 0.8% |
| Preserving agent: | 0.2% |
| Fragrance: | 0.4% |

EXAMPLE 12

Makeup-Removing Emulsion with Sweet Almond Oil

Formula

| Montanov™ 68: | 5% |
|---|---|
| Sweet almond oil: | 5% |
| Water: | qs 100% |
| Inverse latex of Example 1: | 0.3% |
| Glycerol: | 5% |
| Preserving agent: | 0.2% |
| Fragrance: | 0.3% |

EXAMPLE 13

Moisturizing Cream for Greasy Skin

Formula

| Montanov™ 68: | 5% |
|---|---|
| Cetylstearyl octanoate: | 8% |
| Octyl palmitate: | 2% |
| Water: | qs 100% |

-continued

| | |
|---|---|
| Inverse latex of Example 1: | 0.6% |
| Micropearl ™ M 100: | 3.0% |
| Mucopolysaccharides: | 5% |
| Sepicide ™ HB: | 0.8% |
| Fragrance: | 0.3% |

EXAMPLE 14

Alcohol-Free Soothing Aftershave Balm

Formula

| | | |
|---|---|---|
| A | Lipacide ™ PVB: | 1.0% |
| | Lanol ™ 99: | 2.0% |
| | Sweet almond oil: | 0.5% |
| B | Inverse latex of Example 1: | 3.5% |
| C | Water: | qs 100% |
| D | Fragrance: | 0.4% |
| | Sepicide ™ HB: | 0.4% |
| | Sepicide ™ CI: | 0.2% |

EXAMPLE 15

Cream with AHA for Sensitive Skin

Formula

| | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Inverse latex of Example 1: | 1.50% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

EXAMPLE 16

After-Sun Soothing Care

Formula

| | |
|---|---|
| Mixture of lauryl amino acids: | 0.1% to 5% |
| Magnesium potassium aspartate: | 0.002% to 0.5% |
| Lanol ™ 99: | 10.0% |
| Water: | qs 100% |
| Inverse latex of Example 1: | 2.50% |
| Sepicide ™ HB: | 0.3% |
| Sepicide ™ CI: | 0.2% |
| Fragrance: | 0.4% |
| Dye: | 0.03% |

EXAMPLE 17

Makeup-Removing Milk

Formula

| | |
|---|---|
| Sepiperl ™ N: | 3% |
| Primol ™ 352: | 8.0% |

| | |
|---|---|
| Sweet almond oil: | 2% |
| Water: | qs 100% |
| Inverse latex of Example 1: | 0.8% |
| Preserving agent: | 0.2% |

EXAMPLE 18

Fluid Foundation

Formula

| | |
|---|---|
| Simulsol ™ 165: | 5.0% |
| Lanol ™ 84D: | 8.0% |
| Lanol ™ 99: | 5.0% |
| Water: | qs 100% |
| Mineral fillers and pigments: | 10.0% |
| Inverse latex of Example 1: | 1.2% |
| Preserving agent: | 0.2% |
| Fragrance: | 0.4% |

EXAMPLE 19

Antisun Milk

Formula

| | |
|---|---|
| Sepiperl ™ N: | 3.5% |
| Lanol ™ 37T: | 10.0% |
| Parsol ™ MCX: | 5.0% |
| Eusolex ™ 4360: | 2.0% |
| Water: | qs 100% |
| Inverse latex of Example 1: | 1.8% |
| Preserving agent: | 0.2% |
| Fragrance: | 0.4% |

EXAMPLE 20

Eye Contour Gel

Formula

| | |
|---|---|
| Inverse latex of Example 1: | 2.0% |
| Fragrance: | 0.06% |
| Sodium pyrrolidinonecarboxylate: | 0.2% |
| Dow Corning ™ 245 Fluid: | 2.0% |
| Water: | qs 100% |

EXAMPLE 21

Leave-in Care Composition

Formula

| | |
|---|---|
| Inverse latex of Example 1: | 1.5% |
| Fragrance: | qs |
| Preserving agent: | qs |
| Dow Corning ™ X2 8360: | 5.0% |

-continued

| Dow Corning ™ Q2 1401: | 15.0% |
|---|---|
| Water: | qs 100% |

EXAMPLE 22

Slimming Gel

| Inverse latex of Example 1: | 5% |
|---|---|
| Ethanol: | 30% |
| Menthol: | 0.1% |
| Caffeine: | 2.5% |
| Extract of ruscus: | 2% |
| Extract of ivy: | 2% |
| Sepicide ™ HB: | 1% |
| Water: | qs 100% |

EXAMPLE 23

Ultra-Natural Tinted Cream-Gel

Formula

| A | Water: | 10.0% |
|---|---|---|
|   | Butylene glycol: | 4.0% |
|   | PEG-400: | 4.0% |
|   | Pecosil ™ PS100: | 1.5% |
|   | NaOH: | qs pH = 7 |
|   | Titanium dioxide: | 2.0% |
|   | Yellow iron oxide: | 0.8% |
|   | Red iron oxide: | 0.3% |
|   | Black iron oxide: | 0.05% |
| B | Lanol ™ 99: | 4.0% |
|   | Caprylic/capric triglyceride: | 4.0% |
|   | Sepifeel ™ One: | 1.0% |
|   | Inverse latex of Example 1: | 3.0% |
| C | Water: | qs 100% |
|   | Micropearl ™ M305: | 2.0% |
|   | Tetrasodium EDTA: | 0.05% |
|   | Cyclomethicone: | 4.0% |
| D | Sepicide ™ HB: | 0.5% |
|   | Sepicide ™ CI: | 0.3% |
|   | Fragrance: | 0.2% |

Procedure
Prepare the mixture B+C, then add A and then D.

EXAMPLE 24

Care for Greasy Skin

Formula

| A | Micropearl ™ M310: | 1.0% |
|---|---|---|
|   | Inverse latex of Example 1: | 5.0% |
|   | Octyl isononanoate: | 4.0% |
| B | Water: | qs 100% |
| C | Sepicontrol ™ A5: | 4.0% |
|   | Fragrance: | 0.1% |
|   | Sepicide ™ HB: | 0.3% |
|   | Sepicide ™ CI: | 0.2% |
| D | Capigel ™ 98: | 0.5% |
|   | Water: | 10% |

EXAMPLE 25

Cream with AHA

Formula

| A | Montanov ™ 68: | 5.0% |
|---|---|---|
|   | Lipacide ™ PVB: | 1.05% |
|   | Lanol ™ 99: | 10.0% |
| B | Water: | qs 100% |
|   | Gluconic acid: | 1.5% |
|   | TEA (triethanolamine): | 0.9% |
| C | Inverse latex of Example 1: | 1.5% |
| D | Fragrance: | 0.4% |
|   | Sepicide ™ HB: | 0.2% |
|   | Sepicide ™ CI: | 0.4% |

EXAMPLE 26

Non-Greasy Self-Tanning Product for the Face and Body

Formula

| A | Lanol ™ 2681: | 3.0% |
|---|---|---|
|   | Inverse latex of Example 1: | 2.5% |
| B | Water: | qs 100% |
|   | Dihydroxyacetone: | 3.0% |
| C | Fragrance: | 0.2% |
|   | Sepicide ™ HB: | 0.8% |
|   | NaOH (sodium hydroxide): | qs pH = 5 |

EXAMPLE 27

Antisun Milk with Monoï de Tahiti

Formula

| A | Monoï de Tahiti: | 10% |
|---|---|---|
|   | Lipacide ™ PVB: | 0.5% |
|   | Inverse latex of Example 1: | 2.2% |
| B | Water: | qs 100% |
| C | Fragrance: | 0.1% |
|   | Sepicide ™ HB: | 0.3% |
|   | Sepicide ™ CI: | 0.1% |
|   | Parsol ™ MCX: | 4.0% |

EXAMPLE 28

Antisun Care Product for the Face

Formula

| A | Cyclomethicone and dimethiconol: | 4.0% |
|---|---|---|
|   | Inverse latex of Example 1: | 3.5% |
| B | Water: | qs 100% |
| C | Fragrance: | 0.1% |
|   | Sepicide ™ HB: | 0.3% |
|   | Sepicide ™ CI: | 0.21% |
|   | Parsol ™ MCX: | 5.0% |
|   | Titanium mica: | 2.0% |
|   | Lactic acid: | qs pH = 6.5 |

EXAMPLE 29

Self-Tanning Emulsion

Formula

| A | Lanol ™ 99: | 15% |
|---|---|---|
|   | Montanov ™ 68: | 5.0% |
|   | Parsol ™ MCX: | 3.0% |
| B | Water: | qs 100% |
|   | Dihydroxyacetone: | 5.0% |
|   | Monosodium phosphate: | 0.2% |
| C | Inverse latex of Example 1: | 0.5% |
| D | Fragrance: | 0.3% |
|   | Sepicide ™ HB: | 0.8% |
|   | NaOH: | qs pH = 5 |

EXAMPLE 30

Care Cream

| Cyclomethicone: | 10% |
|---|---|
| Inverse latex of Example 1: | 0.8% |
| Montanov ™ 68: | 4.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 31

Care Cream

| Cyclomethicone: | 10% |
|---|---|
| Inverse latex of Example 1: | 0.8% |
| Montanov ™ 68: | 4.5% |
| Perfluoropolymethyl isopropyl ether: | 0.5% |
| Preserving agent: | 0.65% |
| Lysine: | 0.025% |
| EDTA (disodium salt): | 0.05% |
| Pemulen ™ TR1: | 0.2% |
| Glycerol: | 3% |
| Water: | qs 100% |

EXAMPLE 32

Body Milk

Formula

| A | Simulsol ™ 165: | 5.0% |
|---|---|---|
|   | Lanol ™ 1688: | 12.0% |
|   | Lanol ™ 14 M: | 2.0% |
|   | Cetyl alcohol: | 0.3% |
|   | Schercemol ™ OP: | 3% |
| B | Water: | qs 100% |
| C | Inverse latex of Example 1: | 0.35% |
| D | Sepicide ™ CI: | 0.2% |

-continued

| Sepicide ™ HB: | 0.5% |
|---|---|
| Fragrance: | 0.20% |

Procedure

Emulsify B in A at about 75° C.; add C at about 60° C., followed by D at about 30° C.

EXAMPLE 33

Massage Care Gel

Formula

| A | Inverse latex of Example 1: | 3.00% |
|---|---|---|
|   | Water: | 30% |
| B | Sepicide ™ CI: | 0.20% |
|   | Sepicide ™ HB: | 0.30% |
|   | Fragrance: | 0.05% |
| C | Dye: | qs |
|   | Water: | qs 100% |
| D | Micropearl ™ SQL: | 5.0% |
|   | Lanol ™ 1688: | 2% |

Procedure

Prepare A; add B, then C and then D.

EXAMPLE 34

Body Milk

Formula

| A | Sepiperl ™ N: | 3.0% |
|---|---|---|
|   | Glyceryl triheptonate: | 10.0% |
| B | Water: | qs 100% |
| C | Inverse latex of Example 1: | 1.0% |
| D | Fragrance: | qs |
|   | Preserving agent: | qs |

Procedure

Melt A at about 75° C. Emulsify B in A at 75° C. then add C at about 60° C., followed by D.

EXAMPLE 35

Alcohol-Free Soothing Aftershave Balm

Formula

| Mixture of lauryl amino acids: | 0.1% to 5% |
|---|---|
| Magnesium potassium aspartate: | 0.002% to 0.5% |
| Lanol ™ 99: | 2% |
| Sweet almond oil: | 0.5% |
| Water: | qs 100% |
| Inverse latex of Example 1: | 3% |
| Sepicide ™ HB: | 0.3% |
| Sepicide ™ CI: | 0.2% |
| Fragrance: | 0.4% |

EXAMPLE 36

Body Milk

Formula

| | | |
|---|---|---|
| Sepiperl ™ N: | | 3.5% |
| Lanol ™ 37T: | | 8.0% |
| Solagum ™ L: | | 0.05% |
| Water: | | qs 100% |
| Benzophenone-3: | | 2.0% |
| Dimethicone 350 cPs: | | 0.05% |
| Inverse latex of Example 1: | | 0.8% |
| Preserving agent: | | 0.2% |
| Fragrance: | | 0.4% |

EXAMPLE 37

Alcohol-Free Soothing Aftershave Balm

Formula

| | | |
|---|---|---|
| A | Lipacide ™ PVB: | 1.0% |
| | Lanol ™ 99: | 2.0% |
| | Sweet almond oil: | 0.5% |
| B | Inverse latex of Example 1: | 3.5% |
| C | Water: | qs 100% |
| D | Fragrance: | 0.4% |
| | Sepicide ™ HB: | 0.4% |
| | Sepicide ™ CI: | 0.2% |

EXAMPLE 38

Refreshing Aftershave Gel

Formula

| | | |
|---|---|---|
| A | Lipacide ™ PVB: | 0.5% |
| | Lanol ™ 99: | 5.0% |
| | Inverse latex of Example 1: | 2.5% |
| B | Water: | qs 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 39

Cream with AHAs

Formula

| | | |
|---|---|---|
| A | Montanov ™ 68: | 5.0% |
| | Lipacide ™ PVB: | 1.05% |
| | Lanol ™ 99: | 10.0% |
| B | Water: | qs. 100% |
| | Gluconic acid: | 1.5% |
| | TEA (triethanolamine): | 0.9% |
| C | Inverse latex of Example 1: | 1.5% |
| D | Fragrance: | 0.4% |
| | Sepicide ™ HB: | 0.2% |
| | Sepicide ™ CI: | 0.4% |

EXAMPLE 40

Gloss Gel

| | |
|---|---|
| Inverse latex of Example 1: | 1.5% |
| Volatile silicone: | 25% |
| Monopropylene glycol: | 25% |
| Demineralized water: | 10% |
| Glycerol: | qs 100% |

EXAMPLE 41

Slimming Gel

| | |
|---|---|
| Inverse latex of Example 1: | 1.5% |
| Isononyl isononanoate: | 2% |
| Caffeine: | 5% |
| Ethanol: | 40% |
| Micropearl ™ LM: | 2% |
| Demineralized water: | qs 100% |
| Preserving agent, fragrance: | qs |

EXAMPLE 42

Makeup-Removing Milk

| | |
|---|---|
| Simulsol ™ 165: | 4% |
| Montanov ™ 202: | 1% |
| Caprylate/caprate triglyceride: | 15% |
| Pecosil ™ DCT: | 1% |
| Demineralized water: | qs |
| Capigel ™ 98: | 0.5% |
| Inverse latex of Example 1: | 1% |
| Proteol ™ APL: | 2% |
| Sodium hydroxide: | qs pH = 7 |

EXAMPLE 43

Restructuring "Rinse-off" Cream Mask for Stressed and Embrittled Hair

Formula

| | |
|---|---|
| Ketrol ™ T: | 0.5% |
| Pecosil ™ SPP50: | 0.75% |
| N-Cocoyl amino acids: | 0.70% |
| Butylene glycol: | 3.0% |
| Inverse latex of Example 1: | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | qs 100% |

EXAMPLE 44

Antisun Cream

| | |
|---|---|
| Simulsol ™ 165: | 3% |
| Montanov ™ 202: | 2% |
| C12-C15 benzoate: | 8% |
| Pecosil ™ PS 100: | 2% |
| Dimethicone: | 2% |
| Cyclomethicone: | 5% |
| Octyl para-methoxycinnamate: | 6% |
| Benzophenone-3: | 4% |
| Titanium oxide: | 8% |
| Xanthan gum: | 0.2% |
| Butylene glycol: | 5% |
| Demineralized water: | qs 100% |
| Inverse latex of Example 1: | 1.5% |
| Preserving agent, fragrance: | qs |

EXAMPLE 45

Care Gel for Combination Skin

| | |
|---|---|
| Inverse latex of Example 1: | 4% |
| Plant squalane: | 5% |
| Dimethicone: | 1.5% |
| Sepicontrol ™ A5: | 4% |
| Xanthan gum: | 0.3% |
| Water: | qs 100% |
| Preserving agent, fragrance: | qs |

EXAMPLE 46

Hair Lotion

Formula

| | |
|---|---|
| Butylene glycol: | 3.0% |
| Inverse latex of Example 1: | 3% |
| Simulsol ™ 1293: | 3.0% |
| Lactic acid: | qs pH = 6 |
| Sepicide ™ HB: | 0.2% |
| Sepicide ™ CI: | 0.3% |
| Fragrance: | 0.3% |
| Water: | qs 100% |

EXAMPLE 47

Protective and Relaxing Shampoo

Formula

| | |
|---|---|
| Amonyl ™ 675 SB: | 5.0% |
| 28% sodium lauryl ether sulfate: | 35.0% |
| Inverse latex of Example 1: | 3.0% |
| Sepicide ™ HB: | 0.5% |
| Sepicide ™ CI: | 0.3% |
| Sodium hydroxide: | qs pH = 7.2 |
| Fragrance: | 0.3% |
| Dye (FDC Blue 1/Yellow 5): | qs |
| Water: | qs 100% |

EXAMPLE 48

"Leave-on" Protective Product; Anti-Stress Haircare

Formula

| | |
|---|---|
| Ketrol ™ T: | 0.5% |
| Mixture of cocoyl amino acids: | 3.0% |
| Butylene glycol: | 5.0% |
| DC 1501: | 5.0% |
| Composition of Example 1: | 4.0% |
| Sepicide ™ HB: | 0.5% |
| Sepicide ™ CI: | 0.3% |
| Fragrance: | 0.3% |
| Water: | qs 100% |

EXAMPLE 49

Cream with Vitamins

| | |
|---|---|
| Simulsol ™ 165: | 5% |
| Montanov ™ 202: | 1% |
| Caprylic/capric triglycerides: | 20% |
| Vitamin A palmitate: | 0.2% |
| Vitamin E acetate: | 1% |
| Micropearl ™ M305: | 1.5% |
| Inverse latex of Example 1: | 2% |
| Water: | qs 100% |
| Preserving agent, fragrance: | qs |

EXAMPLE 50

Antisun Gel

Formula

| | |
|---|---|
| Inverse latex of Example 1: | 3.00% |
| Sepicide ™ CI: | 0.20% |
| Sepicide ™ HB: | 0.30% |
| Fragrance: | 0.10% |
| Dye: | qs |
| Silica: | 3.00% |
| Water: | qs 100% |
| Silicone oil: | 2.0% |
| Benzophenone-3: | 5.00% |

EXAMPLE 51

Lip Gloss

Formula

| | |
|---|---|
| Inverse latex of Example 1: | 1.50% |
| Schercemol ™ TISC: | 15.00% |
| Vistanol ™ NPGC: | 15.00% |
| Candurin Paprika: | 0.50% |
| Montanox ™ 80: | 1.00% |
| Antaron ™ V216: | 0.90% |
| Apricot flavouring: | 0.20% |
| Sepicide ™ HB: | 0.50% |
| C Maltidex ™ H16322: | qs 100% |

EXAMPLE 52

Pressed Powder for Sunny Climate

Formula

| | |
|---|---|
| Inverse latex of Example 1: | 2.00% |
| Lanol ™ 99: | 12.00% |
| Sepiwhite ™ MSH: | 1.00% |
| Talc: | 33.00% |
| Micropearl ™ M310: | 3.00% |
| Yellow iron oxide: | 0.80% |
| Red iron oxide: | 0.30% |
| Black iron oxide: | 0.05% |
| Mica: | qs 100% |

EXAMPLE 53

Emulsion for Atopic Skin

Formula

| | |
|---|---|
| Arlacel ™ P135: | 2.00% |
| Inverse latex of Example 1: | 1.00% |
| Lanol ™ 1688: | 14.00% |
| Primol ™ 352: | 8.00% |
| Glycerol: | 5.00% |
| Water: | qs 100% |
| Magnesium sulfate: | 0.70% |
| Sepicide ™ HB: | 0.30% |
| Sepicide ™ CI: | 0.20% |
| Micropearl ™ M310: | 5.00% |

EXAMPLE 54

Soothing Antisun Care (Water-in-Silicone)

Formula

| | |
|---|---|
| Inverse latex of Example 1: | 2.00% |
| DC5225C: | 20.00% |
| DC345: | 10.00% |
| Sepicalm ™ VG: | 3.00% |
| Titanium dioxide MT100T: | 5.00% |
| Zinc oxide Z-Cote HP1: | 5.00% |
| Sepicide ™ HB: | 0.30% |
| Fragrance: | 0.05% |
| Sepicide ™ CI: | 0.20% |
| Glycerol: | 5.00% |
| Sodium chloride: | 2.00% |
| Water: | qs 100% |

EXAMPLE 55

Multi-Phase Care

Formula

| | |
|---|---|
| Inverse latex of Example 1: | 3.00% |
| C12-15 alkylbenzoate: | 25.00% |
| Aquaxyl ™: | 3.00% |
| Sepitonic ™ M3: | 1.00% |
| Sepicide ™ HB: | 0.50% |
| Sepicide ™ CI: | 0.30% |
| Water: | qs 100% |

EXAMPLE 56

Self-Tanning Gel

| | |
|---|---|
| Inverse latex of Example 1: | 5% |
| Ethanol: | 30% |
| Dihydroxyacetone: | 4% |
| Erythrulose: | 1% |
| Menthol: | 0.1% |
| Caffeine: | 2.5% |
| Extract of ivy: | 2% |
| Sepicide ™ HB: | 1% |
| Water: | qs. 100% |

EXAMPLE 57

Self-Tanning Antisun Milk

Formula

| | | |
|---|---|---|
| A | Sepiperl ™ N: | 3.0% |
| | Glyceryl triheptonate: | 10.0% |
| | Lipacide ™ PVB: | 0.5% |
| | Inverse latex of Example 1: | 2.2% |
| B | Water: | qs 100% |
| | Dihydroxyacetone: | 5.0% |
| C | Fragrance: | 0.1% |
| | Sepicide ™ HB: | 0.3% |
| | Sepicide ™ CI: | 0.1% |
| | Parsol ™ MCX: | 4.0% |

EXAMPLE 58

Self-Tanning Cream with AHAs

Formula

| | | |
|---|---|---|
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | dihydroxyacetone: | 3.0% |
| | TEA (triethanolamine): | 0.9% |
| C | Inverse latex of Example 1: | 1.5% |
| D | Fragrance: | 0.4% |
| | Sepicide ™ HB: | 0.2% |
| | Sepicide ™ CI: | 0.4% |

EXAMPLE 59

Self-Tanning Cream with AHA for Sensitive Skin

Formula

| Mixture of lauryl amino acids: | 0.1% to 5% |
| --- | --- |
| Magnesium potassium aspartate: | 0.002% to 0.5% |
| Lanol ™ 99: | 2% |
| Montanov ™ 68: | 5.0% |
| Water: | qs 100% |
| Inverse latex of Example 1: | 1.50% |
| Lactic acid: | 1.50% |
| Dihydroxyacetone | 3.5% |
| Triethylamine: | 0.9% |
| Sepicide ™ HB: | 0.3% |
| Sepicide ™ CI: | 0.2% |
| Fragrance: | 0.4% |

EXAMPLE 60

Satin Self-Tanning Moisturizing Emulsion

Formula

| | | |
| --- | --- | --- |
| A | Simulsol ™ 165: | 5.0% |
| | Lanol ™ 1688: | 8.50% |
| | Shea butter: | 2% |
| | Liquid paraffin: | 6.5% |
| | Lanol ™ 14M: | 3% |
| | Lanol ™ S: | 0.6% |
| B | Water: | 66.2% |
| | Dihydroxyacetone | 3% |
| C | Micropearl ™ M 100: | 5% |
| D | Inverse latex of Example 1: | 3% |
| E | Sepicide ™ CI: | 0.3% |
| | Sepicide ™ HB: | 0.5% |
| | Aquaxyl ™: | 5% |
| | Fragrance: | 0.20% |
| | Vitamin E acetate: | 0.20% |
| | Sodium pyrolidinonecarboxylate: | 1% |

The definitions of the commercial products used in the examples are as follows:

Simulsol™ 1293 is hydrogenated and ethoxylated castor oil, with an ethoxylation index equal to 40, sold by the company SEPPIC.

Capigel™ 98 is a liquid thickener based on acrylate copolymer sold by the company SEPPIC.

Ketrol™ T is xanthan gum sold by the company Kelco.

Lanol™ 99 is isononyl isononanoate sold by the company SEPPIC.

DC1501 is a mixture of cyclopentasiloxane and dimethiconol sold by the company Dow Chemical.

Montanov™ 82 is an emulsifier based on cetearyl alcohol and cocoylglucoside.

Montanov™ 68 (cetearyl glucoside) is a self-emulsifying composition as described in WO 92/06778, sold by the company SEPPIC.

Micropearl™ M 100 is an ultra-fine powder with a very soft feel and a matting action, sold by the company Matsumo.

Sepicide™ CI, imidazolidineurea, is a preserving agent sold by the company SEPPIC.

Pemulen™ TR1 is an acrylic polymer sold by Goodrich.

Simulsol™ 165 is self-emulsifying glyceryl stearate sold by the company SEPPIC.

Lanol™ 1688 is an emollient ester with a non-greasy effect sold by the company SEPPIC.

Lanol™ 14M and Lanol® S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Aquaxyl™ is a moisturizer sold by the company SEPPIC.

Schercemol™ OP is an emollient ester with a non-greasy effect.

Lanol™ P is an additive with a stabilizing effect sold by the company SEPPIC.

Parsol™ MCX is octyl para-methoxycinnamate; sold by the company Givaudan.

Sepiperl™ N is a nacreous agent, sold by the company SEPPIC, based on a mixture of alkylpolyglucosides such as those described in WO 95/13863.

Micropearl™ SQL is a mixture of microparticles containing squalane, which is released by the action of massaging; it is sold by the company Matsumo.

Lanol™ 99 is isononyl isononanoate sold by the company SEPPIC.

Lanol™ 37T is glyceryl triheptanoate, sold by the company SEPPIC.

Solagum™ L is a carrageenan sold by the company SEPPIC.

Marcol™ 82 is a liquid paraffin sold by the company Exxon.

Lanol™ 84D is dioctyl malate sold by the company SEPPIC.

Parsol NOX™ is a sunscreen sold by the company Givaudan.

Eusolex™ 4360 is a sunscreen sold by the company Merck.

Dow Corning™ 245 Fluid is cyclomethicone, sold by the company Dow Corning.

Lipacide™ PVB is an acylated wheat protein hydrolysate sold by the company SEPPIC.

Micropearl™ LM is a mixture of squalane, polymethyl methacrylate and menthol, sold by the company SEPPIC.

Sepicontrol™ AS is a mixture of capryloylglycine, sarcosine and extract of Cinnamon zylanicum, sold by the company SEPPIC, such as those described in international patent application PCT/FR98/01313 filed on 23 Jun. 1998.

Lanol™ 2681 is a coconut caprylate/caprate mixture sold by the company SEPPIC.

Montanov™ 202 is an APG/fatty alcohol composition as described in WO 98/47610, sold by the company SEPPIC.

Proteol™ APL is a foaming surfactant sold by the company SEPPIC.

Schercemol™ TISC is an ester (triisostearyl citrate) sold by the company Scher.

Vistanol™ NPGC is an ester (neopentyl glycol dicaprate) sold by the company Sewa Kasei.

Antaron™ V216 is a synthetic polymer (PVP/hexadecene copolymer) distributed by the company Univar.

C Maltidex™ H16322 is a polyol (maltitol syrup) sold by the company Cerestar.

Sepiwhite™ MSH is a depigmenting active agent (undecylenoyl phenylalanine) sold by the company SEPPIC.

DC 345 is a cyclomethicone sold by the company Dow Corning.

DC 5225C is a mixture of cyclopentasiloxane and dimethiconecopolyol sold by the company Dow Corning.

Sepicalm™ VG is a soothing active agent (sodium palmitoylproline) sold by the company SEPPIC.

MT100VT is a micronized titanium dioxide that has undergone a surface treatment (aluminum hydroxide/stearic acid) distributed by the company Unipex.

Z-Cote HP1 is a micronized zinc oxide that has undergone a surface treatment, distributed by Gattefosse.

Candurin Paprika is a mixture of potassium aluminum silicate and iron oxide.

The invention claimed is:

1. A process for preparing a composition comprising an oil phase, an aqueous phase, at least one emulsifying system of the water-in-oil (W/O) type, at least one emulsifying system of the oil-in-water (O/W) type, in the form of a self-invertible latex, said composition comprising from 20% to 70% by weight of a branched or crosslinked polyelectrolyte, wherein said polyelectrolyte is a copolymer (P) of acrylamide with 2-acrylamido-2-methylpropanesulfonic acid partially or totally salified in a form of a salt selected from the group consisting of a sodium salt, a potassium salt and an ammonium salt, said process comprising the following steps:

(a) preparing an aqueous phase (A) comprising acrylamide, 2-acrylamido-2-methylpropanesulfonic acid partially or totally salified in the form of a sodium salt, or of a potassium salt or of an ammonium salt, and, optionally, hydrophilic additives, said preparing of aqueous phase (A) comprising:

(i) forming a solution by placing in water, acrylamide, said optional hydrophilic additives and 2-acrylamido-2-methylpropanesulfonic acid in a form of a salt selected from the group consisting of a sodium salt, a potassium salt and an ammonium salt, (ii) to said solution, adding free 2-acrlyamido-2-methylpropanesulfonic acid and an alkaline agent selected from the group consisting of sodium hydroxide, potassium hydroxide and aqueous ammonia, said free 2-acrlyamido-2-methylpropanesulfonic acid and said alkaline agent being added in alternating portions to said solution such that said solution has a pH that remains greater than 1 and less than 3, to obtain a first aqueous mixture A1 having a pH greater than 1 and less than 3, and (iii) adjusting the pH of said first aqueous mixture A1 to a pH between 5 and 6.5 to obtain said aqueous phase (A) and adding a branching or crosslinking agent;

(b) emulsifying said aqueous phase (A), in an organic phase comprising a surfactant system of the water-in-oil (W/O) type, the oil intended to be present in the final composition, optionally a volatile oil, and optional hydrophobic additives, to form a water-in-oil emulsion (B), said water-in-oil emulsion (B) comprising monomers;

(c) polymerizing the monomers in said water-in-oil emulsion (B), said polymerizing being initiated by introducing a free-radical initiator into said emulsion (B), to form an inverse latex (L1) of said copolymer (P);

optionally, (d) concentrating by distillation of said inverse latex (L1) of said copolymer (P) until said volatile oil has been removed, to form an inverse latex (L2) of said copolymer (P); and (e) introducing an emulsifying system of the oil-in-water (O/W) type at a temperature below 50° C., in said inverse latex (L1) of said copolymer (P), or optionally in said inverse latex (L2) of said copolymer (P), to form a self-invertible inverse latex (L3) of said copolymer (P).

2. The process for preparing a composition as defined in claim 1, wherein the polyelectrolyte comprises:

between 60 mol % and 20 mol % of 2-acrylamido-2-methylpropanesulfonic acid monomer partially or totally salified in a form of a salt selected from the group consisting of a sodium salt, a potassium salt and an ammonium salt, and between 40 mol % and 80 mol % of acrylamide monomer.

3. The process for preparing a composition as defined in claim 2, wherein the polyelectrolyte comprises:

between 50 mol % and 30 mol % of 2-acrylamido-2-methylpropanesulfonic acid monomer partially or totally salified in a form of a salt selected from the group consisting of a sodium salt, a potassium salt and an ammonium salt, and between 50 mol % and 70 mol % of acrylamide monomer.

4. The process for preparing a composition as defined in claim 2, wherein the polyelectrolyte is selected from the group consisting of:

crosslinked copolymers of 2-acrylamido-2-methylpropanesulfonic acid partially salified in the form of the sodium salt and of acrylamide;

crosslinked copolymers of 2-acrylamido-2-methylpropanesulfonic acid partially salified in the form of the ammonium salt and of acrylamide; and crosslinked copolymers of 2-acrylamido-2-methylpropanesulfonic acid partially salified in the form of the potassium salt and of acrylamide.

5. The process for preparing a composition as defined in claim 1, wherein the aqueous mixture A1 obtained at step (a), has a pH value between 1.8 and 2.2.

6. The process for preparing a composition as defined in claim 2, wherein the aqueous mixture A1 obtained at step (a), has a pH value between 1.8 and 2.2.

7. The process for preparing a composition as defined in claim 3, wherein the aqueous mixture A1 obtained at step (a), has a pH value between 1.8 and 2.

8. The process for preparing a composition as defined in claim 3, wherein the polyelectrolyte is selected from the group consisting of:

crosslinked copolymers of 2-acrylamido-2-methylpropanesulfonic acid partially salified in the form of the sodium salt and of acrylamide;

crosslinked copolymers of 2-acrylamido-2-methylpropanesulfonic acid partially salified in the form of the ammonium salt and of acrylamide; and crosslinked copolymers of 2-acrylamido-2-methylpropanesulfonic acid partially salified in the form of the potassium salt and of acrylamide.

* * * * *

UNITED STATES PATENT AND TRADEMARK OFFICE
CERTIFICATE OF CORRECTION

PATENT NO.        : 8,668,915 B2                              Page 1 of 1
APPLICATION NO. : 12/746817
DATED             : March 11, 2014
INVENTOR(S)       : Braun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this

Twenty-ninth Day of September, 2015

Michelle K. Lee
*Director of the United States Patent and Trademark Office*